United States Patent

Kuroda

[11] Patent Number: 5,260,027
[45] Date of Patent: Nov. 9, 1993

[54] METHOD AND APPARATUS FOR AUTOMATICALLY ANALYZING PARTICLES USING PLURAL ANALYZING MODULES

[75] Inventor: Toshiaki Kuroda, Takasagoshi, Japan

[73] Assignee: Toa Medical Electronics Co., Ltd., Kobe, Japan

[21] Appl. No.: 876,425

[22] Filed: Apr. 30, 1992

[30] Foreign Application Priority Data

Jun. 5, 1991 [JP] Japan ............... 3-161159

[51] Int. Cl.⁵ .................. G01N 1/10; G01N 1/16
[52] U.S. Cl. ........................ 422/81; 422/63; 422/67; 422/100; 422/103; 436/43; 436/55; 436/174; 436/179; 436/180; 73/864.84; 73/863.31
[58] Field of Search ........... 422/81, 63, 100, 67, 422/103; 436/180, 179, 174, 52, 53, 54, 43, 55; 73/864.83, 864.84, 864.87, 864.21, 864.22, 863.31, 863.32

[56] References Cited

U.S. PATENT DOCUMENTS

| | | | |
|---|---|---|---|
| 3,990,853 | 11/1976 | Godin | 73/864.84 |
| 3,991,055 | 11/1976 | Godin et al. | 436/150 |
| 4,152,391 | 5/1979 | Cabrera | 73/864.83 |
| 4,512,953 | 4/1985 | Marsoner et al. | 422/67 |
| 4,705,669 | 11/1987 | Tsuji et al. | 422/93 |
| 4,726,237 | 2/1988 | Yung | 73/864.83 |
| 4,726,932 | 2/1988 | Feier et al. | 422/103 |
| 4,746,491 | 5/1988 | Ohlin | 422/103 |
| 4,957,008 | 9/1990 | Proni et al. | 73/864.83 |
| 5,094,961 | 3/1992 | del Valle et al. | 436/180 |

Primary Examiner—James C. Housel
Assistant Examiner—Long V. Le
Attorney, Agent, or Firm—Jones, Tullar & Cooper

[57] ABSTRACT

In blood examinations, first basic items such as the number of red blood cells, the number of white blood cells and the volume of hemoglobins are measured (primary examination), then, on the basis of the results thereof, further specific additional items are measured such as leukocyte classification and measurement of reticulocytes (secondary examination). In this case, the basic items are measured by the basic analyzing module and the results of the measurement are analyzed to judge whether additional items are necessary or not, and only specimens requiring additional items are measured in the additional analyzing module. The additional analyzing module is provided with a temporary sump for temporarily retaining the measuring solution from the measuring solution preparing device. Thus, the blood examination may be done efficiently.

6 Claims, 6 Drawing Sheets

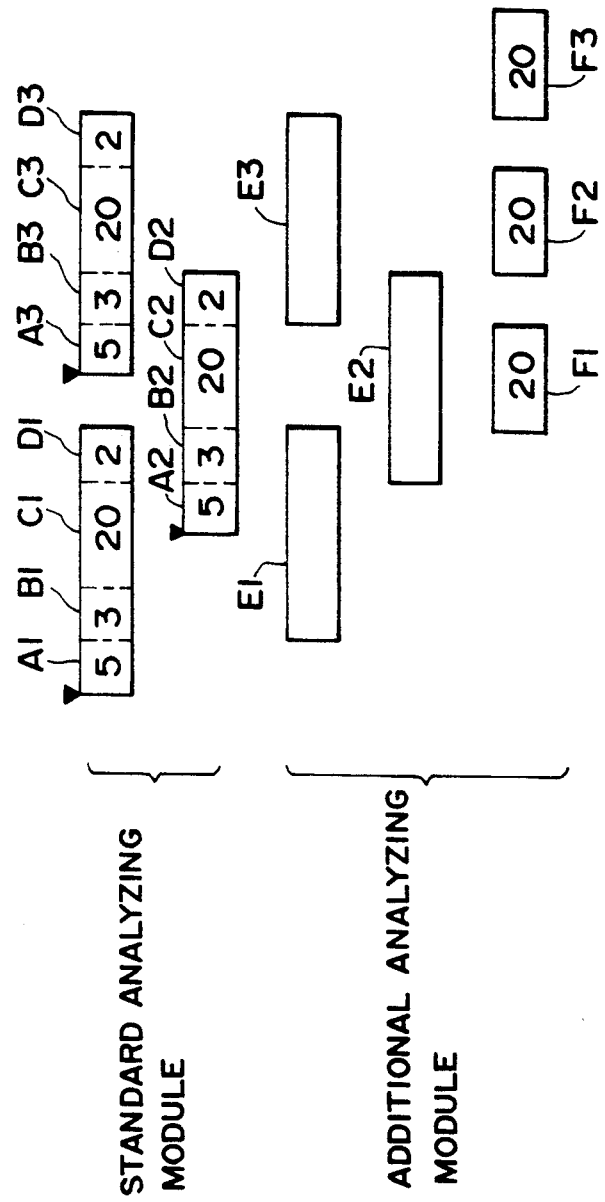

METHOD AND APPARATUS FOR AUTOMATICALLY ANALYZING PARTICLES USING PLURAL ANALYZING MODULES

BACKGROUND OF THE INVENTION

The present invention relates to method and apparatus for automatically analyzing particles for blood examinations, and more particularly to a method for automatically analyzing particles by using plural (a plurality of) analyzing modules differing in measuring items and an apparatus for automatically analyzing particles having these analyzing modules.

A blood cell counter is well known. A fundamental blood cell counter measures basic items such as red blood cells, white blood cells and hemoglobins. Also known are apparatus for classifying leukocytes and apparatus for counting reticulocytes.

In blood examinations, first basic items are measured such as the number of red blood cells, the number of white blood cells and the quantity of hemoglobins (primary examination), then further specific additional items may be measured on the basis of the first results, such as leukocyte classification and measurement of reticulocytes (secondary examination). If the basic items are normal, the secondary examination is not necessary, and only abnormal items require secondary examination. That is, there is a notable difference between the frequency of measurement of basic items and the frequency of measurement of specific items.

In such a two-step measurement, for example, the system is composed as shown in FIG. 1. Numeral 48 is a blood specimen conveying route, and a specimen 52 being mounted on a specimen rack 50 and conveyed through the conveying route 48 is sucked in through a suction unit 42 of a basic examination device (blood cell counter) 40, and measured, then the result of the measurement is produced. A controller (not shown) judges whether the additional examination is necessary or not on the basis of this result. If the additional examination is necessary, the specimen 52 is sucked again through a suction unit 46 of an additional examination device (for example, reticulocyte measuring device) 44, and is measured, then the result of the measurement is produced. If additional examination is not necessary, it directly passes through the conveying route 48.

Concerning such a system, the Japanese Laid-open Patent Hei. 2-163660 is known. In the, apparatus disclosed in this patent, plural analyzing modules are disposed in parallel, specimen circulating means are provided, and the specimen is efficiently sent into each analyzing module.

Thus, when the examination system is built up by merely arranging plural analyzing devices, the system becomes expensive with high costs, and wide space requirements. Yet, by sucking the specimen into each device depending on whether the additional examination is necessary or not, it takes time in sucking each specimen, and a greater quantity of specimen is required. That is, there is much waste and poor efficiency.

OBJECTS AND SUMMARY OF THE INVENTION

It is hence a primary object of the invention to provide a method and apparatus for automatically analyzing particles capable of selecting the analyzing modules depending on the purpose, measuring basic items by a basic analyzing module, judging whether an additional item is necessary or not by analyzing the result of the measurement, and measuring only the specimens requiring the additional item in an additional analyzing module, thereby examining the blood efficiently.

To achieve the above object, the method for automatically analyzing particles of the invention comprises the following steps (a) to (g), that is:

(a) a step of sucking (aspirating) a specimen by suction means (aspirator) of a basic analyzing module, (b) a step of preparing a measuring solution for basic item measurement and a measuring solution for additional item measurement, (c) a step of measuring the basic items after transferring the measuring solution for basic item measurement into a measuring unit, (d) a step of transferring the measuring solution for additional item measurement into a temporary sump of an additional analyzing module, (e) a step of analyzing the measuring results of basic items, and judging whether the measurement of additional items is necessary or not, (f) a step of temporarily retaining the measuring solution for additional item measurement in the temporary sump during the step of basic item measurement (temporary retention step), and disposing the measuring solution for additional item measurement if additional item measurement is not necessary, or transferring to a measuring unit if additional item measurement is necessary, thereby measuring the additional items, after judgement of the necessity of additional item measurement, and (g) a step of sucking (aspirating) a next specimen after the measuring step of the basic item, without waiting for the end of the measuring step of additional items.

Another method of the invention comprises the following steps (a) to (g), that is:

(a) a step of sucking (aspirating) a specimen by suction (aspiration) means of a basic analyzing module, (b) a step of preparing a measuring solution for basic item measurement and a measuring solution for additional item measurement, (c) a step of measuring the basic items after transferring the measuring solution for basic item measurement into a measuring unit, (d) a step of transferring the measuring solution for additional item measurement into either one of a first temporary sump and a second temporary sump of an additional analyzing module, (e) a step of analyzing the measuring results of basic items, and judging whether the measurement of additional items is necessary or not, (f) a step of temporarily retaining the measuring solution for additional item measurement in either one of the first temporary sump and second temporary sump during the step of basic item measurement, and disposing the measuring solution for additional item measurement if additional item measurement is not necessary, or transferring to a measuring unit if additional item measurement is necessary, thereby measuring the additional items, after judging the necessity of additional item measurement, and (g) a step of performing a suction step of the next specimen without waiting for the end of the additional item measurement, and performing a suction (aspiration) step of the next specimen without waiting for the end of the basic item measurement, and retaining the measuring solution for an additional item measurement in either one of the first temporary sump and second temporary sump.

This method is thus intended to suck (aspirate) the next specimen during the step of basic item measurement, and retain the prepared measuring solution in the first temporary sump or second temporary sump, which reduces specimen waste and shortens the time required for examination.

In a further different method of the invention, a step of setting (a) a measurement of basic items and a measurement of additional items on the basis of the result of the judgement thereof, (b) a measurement of basic items only, and (c) a measurement of basic items and a measurement of additional items is provided for each specimen before the start of examination, and in the case of (a), the above method of the invention is applied, in the case of (b), only the basic items are measured without measuring the additional items, and in the case of (c), aside from the measurement of the basic items, additional items are measured unconditionally.

An apparatus for automatically analyzing particles of the invention comprises plural analyzing modules differing in measuring items, a control device for controlling the function of the analyzing modules, and an analyzing device for analyzing data from the analyzing modules wherein one of the plural analyzing modules is the basic analyzing module having a measuring unit for measuring basic items, and the other analyzing module is the additional analyzing module having a measuring unit for measuring additional items, the basic analyzing module has measuring solution preparing means for preparing a measuring solution for the basic analyzing module and a measuring solution for the additional analyzing module, and the additional analyzing module has a temporary sump for temporarily retaining the measuring solution for the additional analyzing module from the measuring solution preparing means.

In the above apparatus, practically, the measuring solution preparing means should be preferably composed of a sampling valve as a sample quantitative picking means for distributing a sample composed of plural elements in slices, a sample suction probe connected to the sampling valve, sample suction means connected to the sampling valve, liquid dispensing means for basic analyzing module connected to the sampling valve, and liquid dispensing means for an additional analyzing module connected to the sampling valve. In the sampling valve, the original sample is quantitatively taken separately for the basic analyzing module and for an additional analyzing module.

Also, in this apparatus, the second temporary sump may be additionally installed at the upstream side of the measuring unit of the additional analyzing module. The second temporary sump and the first temporary sump may be installed either in series or in parallel.

The measuring solution, meanwhile, refers to the solution treated and adjusted from the original sample to be measured so as to be suited for measurement in each measuring unit. For example, the measuring solution may be simply a diluted solution of the sample, or a solution of sample mixed with a hemolyzing agent or dyestuff.

The additional analyzing module may be selected depending on the purpose of the examination. First, suction means such as a suction pump operates to suck the sample, and is introduced into the sample quantitative picking means built in the basic analyzing module. The sample is quantitatively taken separately for the basic analyzing module and for an additional analyzing module.

Next, the liquid dispensing means operate, and the quantitatively taken sample is transferred, together with each solution, into the measuring unit of the basic analyzing module and the temporary sump of the additional analyzing module.

In the measuring unit of the basic analyzing module, basic items are measured. In this period, the measuring solution transferred to the temporary sump in the additional analyzing module remains there. After measurement of the basic items, on the basis of the result, it is judged whether measurement of additional items is necessary or not in the analyzing device. More specifically, when normal, measurement of additional items is not necessary, and if an abnormality is suspected, it is judged necessary to measure the additional items. If not necessary, the measuring solution kept in the temporary sump is disposed of. If necessary, it is sent into the measuring unit, and the additional items are measured.

When measurement of basic items is over, whether the additional items are measured or not, the next sample is sucked in. In the case of measurement of additional items, the action of measurement of additional items and suction of the next sample overlap.

When a first temporary sump and a second temporary sump are provided, the action is the following. That is, not only is there overlapping in the operating step of the basic analyzing module and the measuring step of the additional analyzing module, but there is also overlapping in the steps of the basic analyzing module, overlapping takes place more efficiently and the waiting time is eliminated, so that the examination time may be shortened.

In the apparatus, since the action of the basic analyzing module overlaps, by installing further the second temporary sump in the additional analyzing module, the measuring solution for the additional analyzing module may be retained for the portion of two specimens. The measuring solutions retained for two specimens are transferred sequentially into the measuring unit to be measured.

BRIEF DESCRIPTION OF THE DRAWINGS

FIG. 6 is a time chart of the operation in the apparatus shown in FIG. 4.

DETAILED DESCRIPTION OF THE PREFERRED EMBODIMENTS

Figure 1:
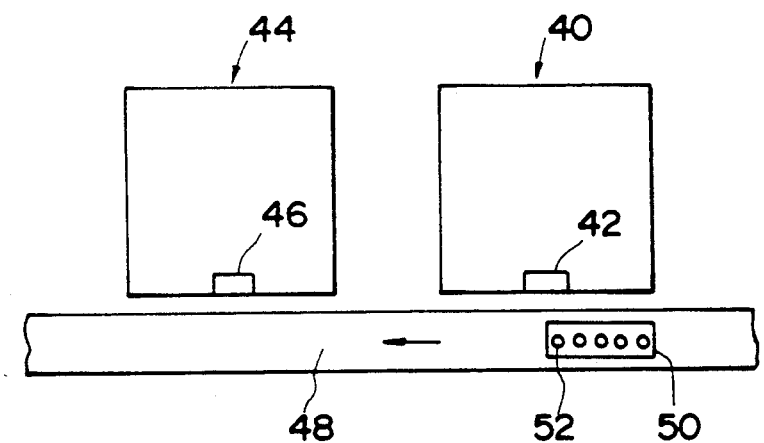
FIG. 1 is a schematic diagram showing an example of a conventional apparatus for automatically analyzing particles.

Referring now to the drawings, some of the preferred embodiments of the invention are described in detail below.

Figure 2:
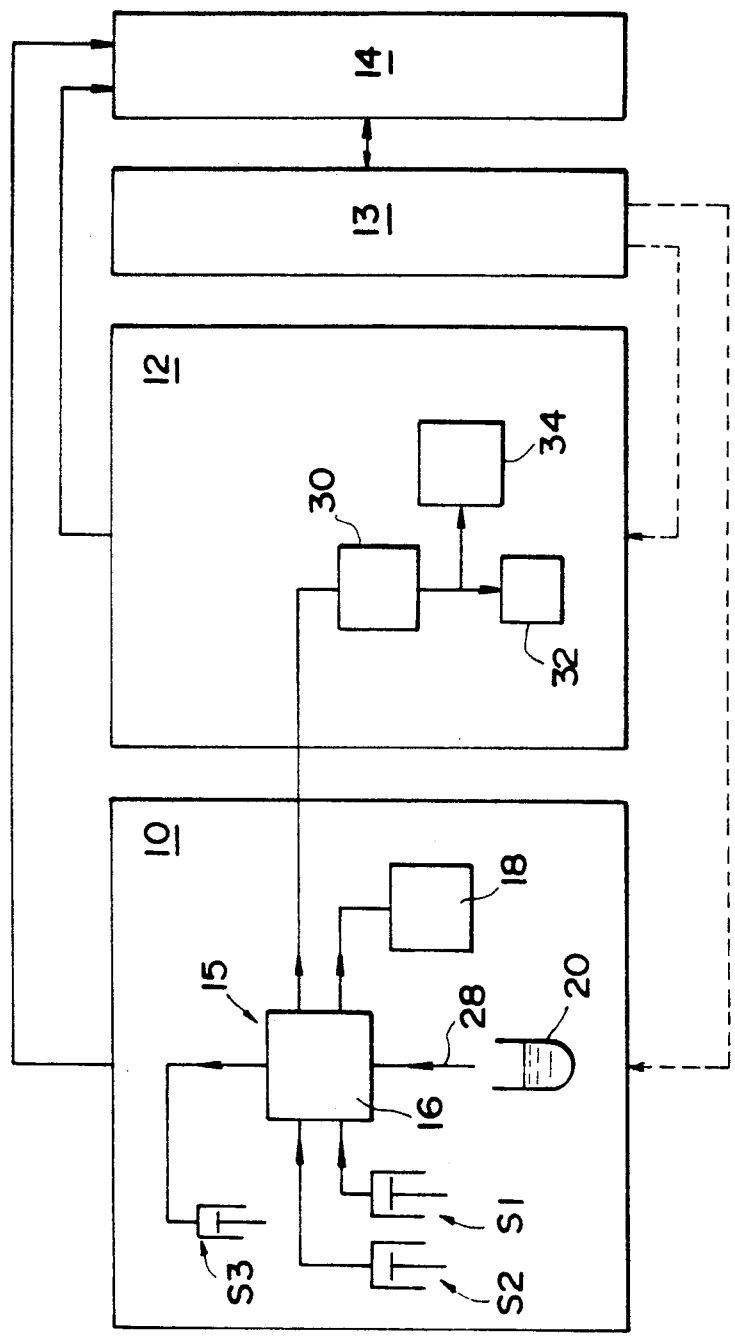
FIG. 2 is a system diagram showing an embodiment of an apparatus for automatically analyzing particles of the invention.
Figure 3:
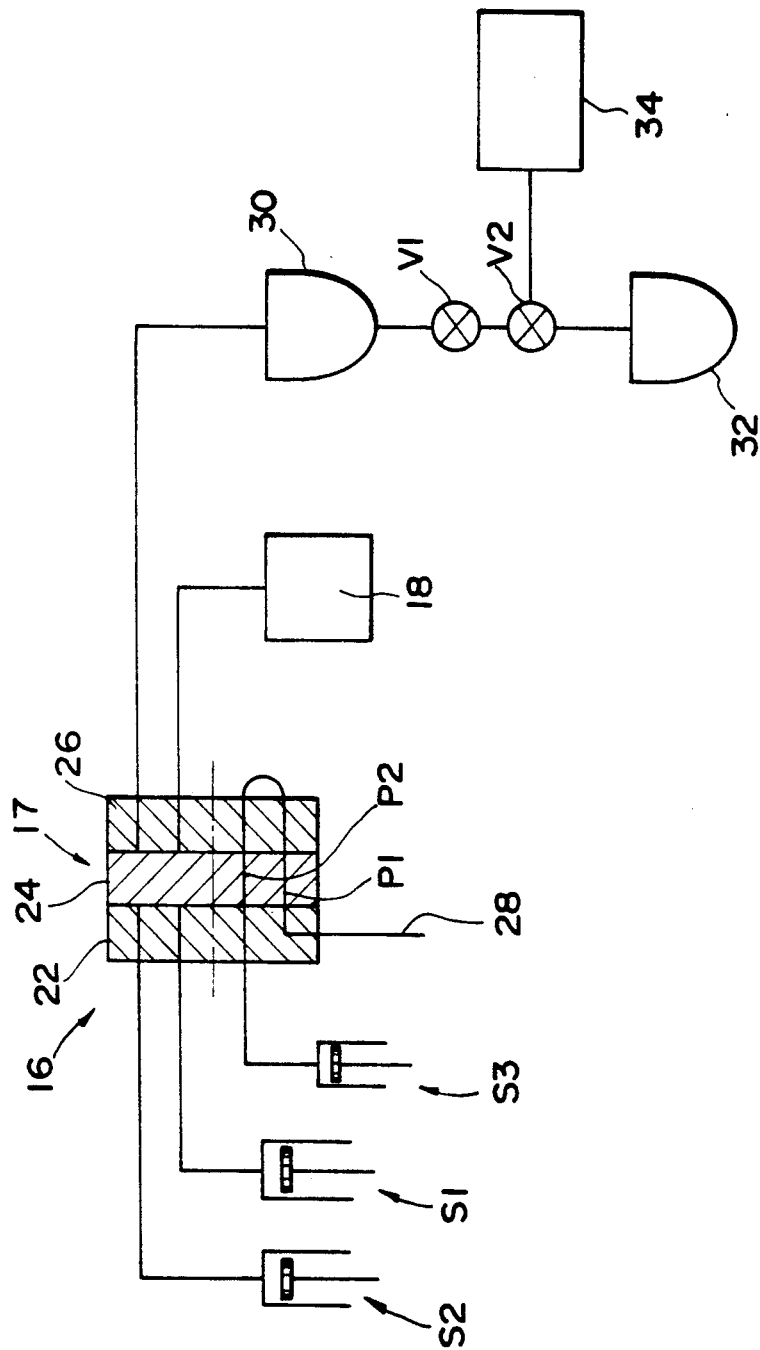
FIG. 3 is a system diagram showing an example of the measuring solution preparing means and its surroundings in FIG. 2.

The method for automatically analyzing particles according to one aspect of the invention comprises, by reference to FIG. 2 and FIG. 3, the following steps (a) to (g), that is:

(a) a step of sucking (aspirating) a specimen by suction means (aspirator) of a basic analyzing module 10, (b) a step of preparing a measuring solution for basic item measurement and a measuring solution for additional item measurement, (c) a step of measuring the basic items after transferring the measuring solution for basic item measurement into a measuring unit 18, (d) a step of transferring the measuring solution for additional item measurement into a temporary sump 30 of an additional analyzing module 12, (e) a step of analyzing the measuring results of basic items, and judging whether the measurement of the additional items is necessary or not, (f) a step of temporarily retaining the measuring solution for additional item measurement in the temporary sump 30 during the step of basic item measurement (temporary retention step), and disposing the measuring solution for additional item measurement if additional item measurement is not necessary, or transferring to a measuring unit 34 if additional item measurement is necessary, thereby measuring the additional items, after judging the necessity of additional item measurement, and (g) a step of sucking (aspirating) a next specimen after the measuring step of the basic item, without waiting for the end of the measuring step of the additional items.

Figure 4:
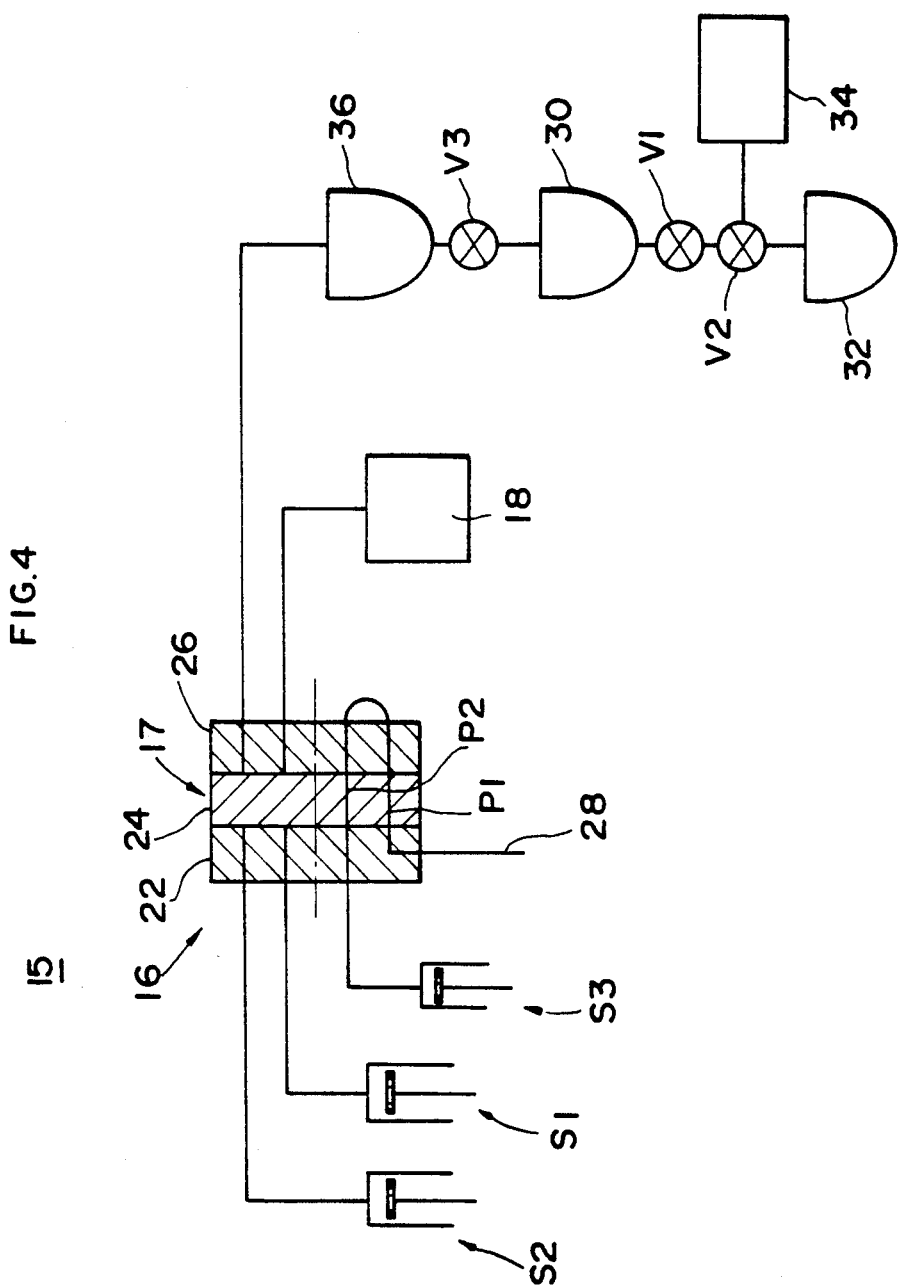
FIG. 4 is a system diagram showing another embodiment of the essential parts in the apparatus of the invention.

The invention may also comprise, by reference to FIG. 2 and FIG. 4, the following steps (a) to (g), that is:

(a) a step of sucking (aspirating) a specimen by suction (aspiration) means of a basic analyzing module 10, (b) a step of preparing a measuring solution for basic item measurement and a measuring solution for additional item measurement, (c) a step of measuring the basic items after transferring the measuring solution for basic item measurement into a measuring unit 18, (d) a step of transferring the measuring solution for additional item measurement into either one of a first temporary sump 30 and a second temporary sump 36 of an additional analyzing module, (e) a step of analyzing the measuring results of basic items, and judging whether the measurement of the additional items is necessary or not, (f) a step of temporarily retaining the measuring solution for additional item measurement in either one of the first temporary sump 30 and second temporary sump 36 during the step of basic item measurement, and disposing the measuring solution for additional item measurement if additional item measurement is not necessary, or transferring to a measuring unit 34 if additional item measurement is necessary, thereby measuring the additional items, after judging the necessity of additional item measurement, and (g) a step of performing a suction step of the next specimen without waiting for the end of the additional item measurement, and performing a suction (aspiration) step of the next specimen without waiting for the end of the basic item measurement, and retaining the measuring solution for additional item measurement in either one of the first temporary sump 30 and second temporary sump 36.

This method is thus intended to suck (aspirate) the next specimen during the step of basic item measurement, and retain the prepared measuring solution in the first temporary sump 30 or second temporary sump 36, which reduces specimen waste and shortens the time required for examination.

The invention may also comprise, a step of setting (a) a measurement of basic items and a measurement of additional items on the basis of the result of a judgement thereof, (b) a measurement of basic items only, and (c) a measurement of basic items and measurement of additional items is provided for each specimen before the start of examination, and in the case of (a), the above method of the invention is applied, in the case of (b), only the basic items are measured without measuring the additional items, and in the case of (c), aside from the measurement of the basic items, additional items are measured unconditionally.

An apparatus for automatically analyzing particles according to the invention comprises, as shown in FIG. 2 and FIG. 3, plural analyzing modules 10, 12 differing in measuring items, a control device 13 for controlling the function of the analyzing modules 10, 12, and an analyzing device 14 for analyzing data from the analyzing modules 10, 12, wherein one of the plural analyzing modules is the basic analyzing module 10 having a measuring unit 18 for measuring basic items, and the other analyzing module is the additional analyzing module 12 having a measuring unit 34 for measuring additional items, the basic analyzing module 10 has measuring solution preparing means 15 for preparing a measuring solution for the basic analyzing module and a measuring solution for the additional analyzing module, and the additional analyzing module 12 has a temporary sump 30 for temporarily retaining the measuring solution for the additional analyzing module from the measuring solution preparing means 15.

In the above apparatus, practically, the measuring solution preparing means 15 preferably comprises a sampling valve 17 as a sample quantitative picking, or sampling means for distributing a segmented liquid sample composed of plural elements in slices, a sample suction probe 28 connected to the sampling valve 17, sample suction means S3 connected to the sampling valve 17, liquid dispensing means S1 for basic analyzing module connected to the sampling valve 17, and liquid dispensing means S2 for additional analyzing module connected to the sampling valve 17. In the sampling valve 17, the original sample is quantitatively taken separately for the basic analyzing module and for the additional analyzing module.

Also, in this apparatus, the second temporary sump 36 may be additionally installed at the upstream side of the measuring unit 34 of the additional analyzing module 12. The second temporary sump 36 and the first temporary sump 30 may be installed either in series or in parallel.

The measuring solution, meanwhile, refers to the solution treated and adjusted from the original sample to be measured so as to be suited to measurement in each measuring unit. For example, the measuring solution may be a simply diluted solution of the sample, or a solution of sample mixed with hemolyzing agent or dyestuff.

The additional analyzing module may be selected depending on the purpose of the examination. First, suction means S3, such as a suction pump, operates to suck in the sample, and is introduced into the sample quantitative picking or sampling means 16 built in the basic analyzing module 10. The sample is quantitatively taken separately for the basic analyzing module and for the additional analyzing module.

Next, the liquid dispensing means S1, S2 operate, and the quantitatively taken sample is transferred, together with each solution, into the measuring unit 18 of the basic analyzing module 10 and the temporary sump 30 of the additional analyzing module 12.

In the measuring unit 18 of the basic analyzing module, basic items are measured. In this period, the measuring solution transferred to the temporary sump 30 in the additional analyzing module remains there. After the measurement of the basic items, and on the basis of the results received, it is judged whether measurement of additional items is necessary or not in the analyzing device 14. More specifically, when normal, measurement of the additional items is not necessary, and if an abnormality is suspected, it is judged necessary to measure the additional items. If not necessary, the measuring solution kept in the temporary sump 30 is disposed of. If necessary, it is sent into the measuring unit 34, and the additional items are measured.

When measurement of the basic items is over, whether the additional items are measured or not, the next sample is sucked in. In the case of a measurement of a additional items, the measurement of the additional items and suction of the next sample overlap.

As shown in FIG. 4, when the first temporary sump 30 and the second temporary sump 36 are provided, the action is as follows. That is, not only overlapping of the operating step of the basic analyzing module and the measuring step of the additional analyzing module occur, but also overlapping of the steps of the basic analyzing module. As a result overlapping takes place more efficiently and the waiting time is eliminated, so that the examination time is shortened.

In the apparatus shown in FIG. 4, since overlap occurs in the action of the basic analyzing module, by further installing the second temporary sump 36 in the additional analyzing module, the measuring solution for the additional analyzing module may be retained for the portion of two specimens. The measuring solutions retained for two specimens are transferred sequentially into the measuring unit 34 to be measured.

FIG. 2 is a schematic diagram showing an embodiment of an apparatus for automatically analyzing particles of the invention.

Numeral 10 shows a basic analyzing module for measuring the basic items, 12 is an additional analyzing module for measuring the additional items, 13 is a control device for controlling the action of both, 14 is an analyzing device for analyzing the data, and 15 is means for preparing measuring solutions for the basic analyzing module and for the additional analyzing module, which comprises means 16 for quantitatively taking a blood sample, suction means (aspirator) S3 such as a sample suction (aspiration) probe 28 or suction (aspiration) pump as the guide route for introducing the blood sample into the sample quantitative picking means 16, and liquid dispensing means S1, S2 for dispensing a specific volume of liquid for diluting at a specific dilution factor, and transferring the determined sample.

A practical example of a sample quantitative picking means 16 is shown in FIG. 3. Numeral 17 is a sampling valve comprising a plurality of (three, for example, in this embodiment) elements 22, 24, 26 possessing passages for passing liquid such as a sample, being designed to separate the specimen into slices and sample quantitatively as the movable element 24 held by stationary elements 22, 26 at both sides rotates. Penetration passages P1, P2 disposed in the movable element 24 are passages for determining samples quantitatively. In one passage P1, a sample for the basic analyzing module is picked quantitatively, and in the other passage P2, the sample for the additional analyzing module is picked quantitatively. The sampling valve 17 is connected with a sample suction probe (needle-like thin tube) 28 as a guide passage, sample suction means S3 such as a sample suction pump, and a liquid dispensing means S1, S2 such as pumps for dispensing liquid for diluting (diluting liquid). The liquid dispensing means S1 for the basic analyzing module, and the other liquid dispensing means S2 is for the additional analyzing module.

Figure 5:
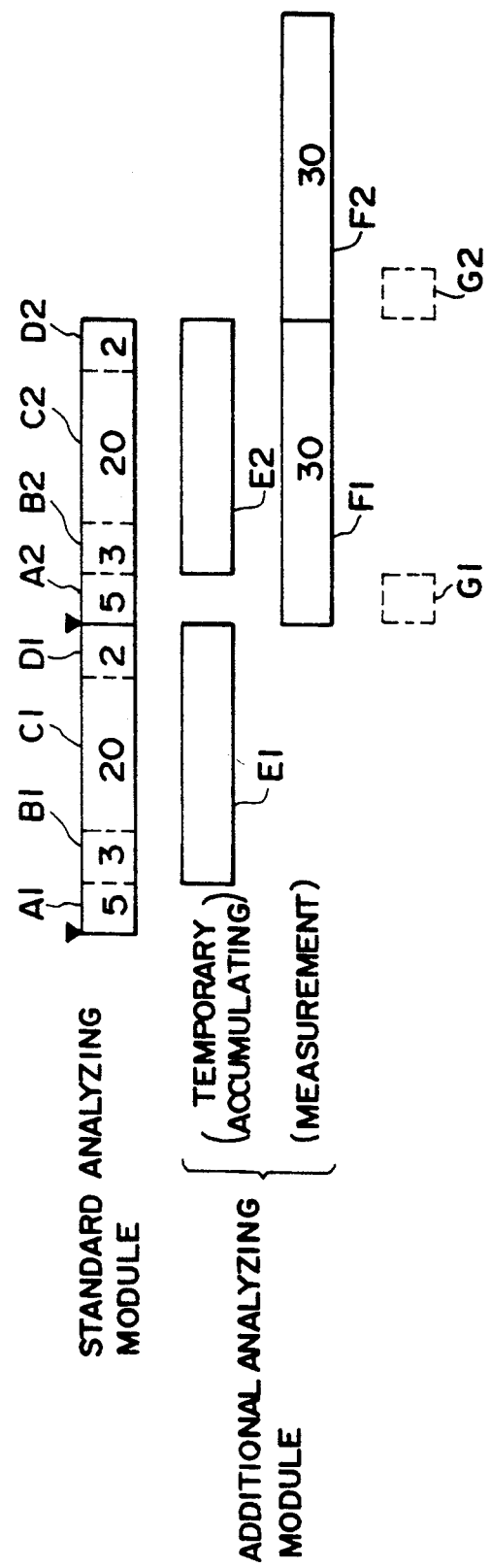
FIG. 5 is a time chart of the operation in the apparatus shown in FIG. 3.

The operation is described herein while referring also to the time chart of operation in FIG. 5. The numerical value in FIG. 5 denotes the time (in seconds).

(1) Sample suction (aspiration) step (A1)

The blood sample (specimen 1) put in the specimen container 20 is introduced into passages P1, P2 of the sampling valve 17 by the suction action of the suction means S3.

(2) Measuring solution preparing step (B1)

As the movable element 24 rotates, the sample in the passages P1, P2 is separate into slices, and as the liquid dispensing means S1 further operates, the sample in the passage P1 is sent into the measuring unit 18 of the basic analyzing module 10 together with a diluting liquid, and as the liquid dispensing means S2 operates, the sample in the passage P2 is transferred to the temporary sump 30 of the additional analyzing module 12 together with the diluting liquid. As a practical example of the temporary sump 30, a chamber 30 is used, and the chamber 30 is connected to a waste liquid chamber 32 for keeping the discharged liquid through valves V1, V2, and a measuring unit 34 for measuring the additional items. The measuring solution is not limited to a mere diluted solution of blood sample, but also includes solutions mixed with a hemolyzing agent, dyestuff, or the like depending on the specification.

(3) Basic module measuring step (C1)

The basic items are, for example, the number of red blood cells (RBC), the number of white blood cells (WBC), the quantity of hemoglobins (HGB), the hematocrit level (HCT), the mean red corpuscular volume (MCV), the quantity of mean red corpuscular hemoglobin (MCH), the mean red corpuscular hemoglobin concentration (MCHC), and the number of platelets (PLT). These eight basic items are measured in the measuring unit 18.

(4) Temporary retaining step (E1)

On the other hand, the measuring solution for the additional analyzing module is held in the temporary sump 30.

(5) Judging step (D1)

When the measurement of the basic items is over, the result is analyzed by the analyzing unit 14, and it is judged whether further additional examination is necessary or not.

(6) Disposing step (G1)

When additional examination is not necessary, the measuring solution in the temporary sump 30 is directly disposed into the waste liquid chamber 32.

(7) Additional analyzing module measuring step (F1)

If additional measurement is necessary, the measuring solution is transferred from the temporary sump 30 into the measuring unit 34, and the additional item, for example, reticulocyte is measured. As the additional item, meanwhile, if classification and counting of leukocytes are desired, such analyzing module should be used as an additional analyzing module.

(8) Step of next specimen (A2 to G2)

After the judging step (D1), without waiting for the end of the measuring step (F1) of the additional analyzing module, the basic analyzing module 10 starts processing on next specimen. The steps A2 to G2 on specimen 2 correspond to steps A1 to G1 of specimen 1, respectively.

Thus, by disposing the temporary sump 30 for provisionally holding the measuring solution in the additional analyzing module, the measuring step (F1) of the additional item and the suction or other operation of the next specimen (A2, B2, C2, D2, E2) may be overlapped in action, so that the processing time may be shortened notably. Concerning FIG. 5, the time is cut almost in half.

If the measuring step F1 of the additional analyzing module is longer in time than the total of steps A1 to D1 of the basic analyzing module, in spite of the overlapping action, as far as there is only one measuring unit in the additional analyzing module, the sample suction cycle (indicated by the "▼" mark in FIG. 5) is restricted by the measuring step F1, and the processing time for one specimen cannot be shortened furthermore.

In FIG. 5, if the time required for the measuring step F1 is shorter than the time required for all of steps A1 to D1, by slightly overlapping the processing step of the specimen 1 of the basic analyzing module and the processing step of the specimen 2, the sample suction cycle may be also shortened along with the shortening of the measuring step F1.

However short the measuring step F1 of the additional analyzing module may be, since there is only one temporary sump 30, the shortening is limited in a range so that the temporary retaining steps E1, E2 may not overlap each other. If desired to shorten the time further, another temporary sump must be disposed in the additional analyzing module so as to overlap the temporary retaining steps E1, E2.

Accordingly, a second temporary sump is disposed between the sample preparing means 15 and the measuring unit 34, that is, before (at the upstream side of) the measuring unit 34. An example is shown in FIG. 4. The second temporary sump 36 is disposed in series before the first temporary sump 30. Between the both temporary sumps 30, 36, a valve V3 is disposed, which controls whether or not to pass the measuring solution. The measuring solution of specimen 1 is put into the chamber 30 through the chamber 36, and is held for a specific time. The measuring solution of specimen 2 is held in the chamber 36. When the measuring solution of specimen 1 is transferred to the measuring unit 34, the measuring solution of specimen 2 is transferred from the chamber 36 to chamber 30. The chamber 36 is then empty, and it is ready to hold the measuring solution of specimen 3. In this way, the measuring solutions move along the chambers sequentially, so that the measuring solutions of two specimens may be held and maintained at the same time.

The second temporary sump 36 may also be disposed parallel to the first temporary sump 30, so that the measuring solutions may be held alternately.

FIG. 6 is a time chart showing an example of overlap when the second temporary sump 36 is used. The numerals in FIG. 6 denote the time (seconds). The temporary retaining steps E1 and E2, and E2 and E3 of the additional analyzing module are overlapped in action.

Explained hereabove is the procedure of measuring the basic items in the first place, then measuring additional items depending on the results obtained.

As to other additional functions, three points may be instructed before start of examination, that is: 1. measurement of the basic items and measurement of the additional items on the basis of the judgement results (the function explained so far), 2. measurement of the basic items only, and 3. measurement of the basic items and the additional item unconditionally. As a result, the function becomes flexible as an examination system, which is very useful. It will be more useful if instructed individually for specimens. In such a case, it is necessary to attach a bar code label or other identifying object to the specimen container, and install means for reading the identifying object at the analyzing module side.

Being thus constructed, the invention brings about the following effects.

(1) An apparatus for automatically analyzing particles of the invention having plural analyzing modules, and the analyzing modules can be selected, so that the measuring items may be extended, and the most appropriate system may be built up depending on the purpose and necessity of the examination.

(2) The additional analyzing module is provide with means for temporarily retaining the solution for measurement, and overlap operation is enabled. Consequently, it is enough to drawn in a sample only once, and sample waste is eliminated, and the time shortened.

(3) After the results of the measurement of the basic analyzing module is disclosed, it is decided whether to dispose of the solution or to measure additional items and. Therefore, only necessary specimens may be picked up and inspected additionally without slowing down the processing speed, which results in economy and efficiences.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An apparatus for automatically analyzing particles using a plurality of analyzing modules, said apparatus comprising:

a plurality of analyzing modules for measuring differing measuring items, one of said plurality of analyzing modules comprises a basic analyzing module having a measuring unit for measuring basic items, and the others of said plurality of analyzing modules comprising additional analyzing modules each having valve means and a measuring unit for measuring additional items, said basic analyzing module further having measuring solution preparing means for preparing a measuring solution for the basic analyzing module and a measuring solution for the additional analyzing modules, said additional analyzing modules each have a temporary sump for temporarily retaining its measuring solution, and each said temporary sump being disposed upstream of its respective measuring unit and connected to its respective measuring unit through said valve means, a control means for controlling the function of the analyzing modules, and an analyzing device for analyzing data from the analyzing modules, wherein said control means serving to initiate operation of said additional analyzing modules based on the analysis performed by said basic analyzing module said analyzing device such that the measuring solution in any one of said temporary sumps is disposed of or transferred to its respective measuring unit for measuring additional items.

2. The apparatus according to claim 1, wherein said measuring solution preparing means includes a quantitative sampling means comprising a sampling valve having a plurality of elements for separating a sample liquid into slices, a sample suction probe connected to the sampling valve, and sample suction means connected to the sampling valve, said apparatus further comprising first liquid dispensing means connected to the sampling valve and said basic analyzing module, and second liquid dispensing means connected to the sampling valve and said additional analyzing modules.

3. The apparatus according to claim 1, wherein at least one additional analyzing module having a second temporary sump and a valve additionally disposed at the upstream side of its respective measuring unit.

4. The apparatus according to claim 2, wherein at least one additional analyzing module having a second temporary sump and a valve additionally disposed at the upstream side of the measuring unit.

5. The apparatus according to claim 1, wherein for each sample said control means effects one of the following:
   a) measurement of basic items and measurement of additional items on the basis of the result of a judgement made relative to the measurement of the basic items;
   b) measurement of basic items only; and
   c) measurement of basic elements and measurement of additional elements.

6. The apparatus according to claim 2, wherein for each sample said control means effects one of the following:
   a) measurement of basic items and measurement of additional items on the basis of the result of a judgement made relative to the measurement of the basic items;
   b) measurement of basic items only; and
   c) measurement of basic elements and measurement of additional elements.

* * * * *

UNITED STATES PATENT AND TRADEMARK OFFICE
CERTIFICATE OF CORRECTION

PATENT NO. : 5,260,027

DATED : November 9, 1993

INVENTOR(S) : Toshiaki Kuroda

It is certified that error appears in the above-identified patent and that said Letters Patent is hereby corrected as shown below:

Claim 1, column 11, line 15, between "module" and "said" --and-- should be inserted.

Signed and Sealed this

Nineteenth Day of April, 1994

Attest:

BRUCE LEHMAN

Attesting Officer

Commissioner of Patents and Trademarks